(12) United States Patent
Cornish et al.

(10) Patent No.: US 6,491,648 B1
(45) Date of Patent: Dec. 10, 2002

(54) GUIDEWIRE WITH TAPERED FLEXIBLE CORE SEGMENT

(75) Inventors: Wayne E. Cornish, Fallbrook, CA (US); Mark T. Richardson, Escondido, CA (US); Lawrence E. Brennan, Temecula, CA (US); Marc M. Jalisi, Temecula, CA (US); David M. Anderson, Temecula, CA (US); Mo Jafari, Murrieta, CA (US); Sepehr Fariabi, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/748,299

(22) Filed: Dec. 21, 2000

Related U.S. Application Data

(63) Continuation-in-part of application No. 09/224,451, filed on Dec. 31, 1998.

(51) Int. Cl.[7] ................................................. A61B 5/00
(52) U.S. Cl. ......................................................... 600/585
(58) Field of Search ................................ 600/585, 434, 600/435; 604/167, 170, 280, 282

(56) References Cited

U.S. PATENT DOCUMENTS

| 3,452,742 | A | | 7/1969 | Muller ............................ 128/2 |
| 4,003,369 | A | * | 1/1977 | Helina et al. ................. 600/585 |
| 4,846,186 | A | * | 7/1989 | Box et al. ..................... 600/585 |
| 4,854,330 | A | * | 8/1989 | Evans et al. .................. 600/585 |
| 4,867,173 | A | * | 9/1989 | Leoni ............................ 600/585 |
| 5,429,139 | A | * | 7/1995 | Sauter .......................... 600/585 |
| 5,497,783 | A | | 3/1996 | Urick et al. .................. 128/772 |
| 5,788,654 | A | * | 8/1998 | Schwager ..................... 600/585 |

FOREIGN PATENT DOCUMENTS

| WO | 9724978 | 7/1997 |

* cited by examiner

*Primary Examiner*—Max Hindenburg
(74) *Attorney, Agent, or Firm*—Fulwider Patton Lee & Utecht, LLP

(57) ABSTRACT

A guidewire for guiding a medical device within a patient which has an elongate core member with a flexible body member disposed about and secured to a distal core section and a flexible core segment or flexible core segment which has a first pair of opposed faces which define a first transverse dimension that tapers from a first value to a second larger value and a second pair of opposed faces which define a second transverse dimension that tapers from a first value to a second smaller value.

36 Claims, 3 Drawing Sheets

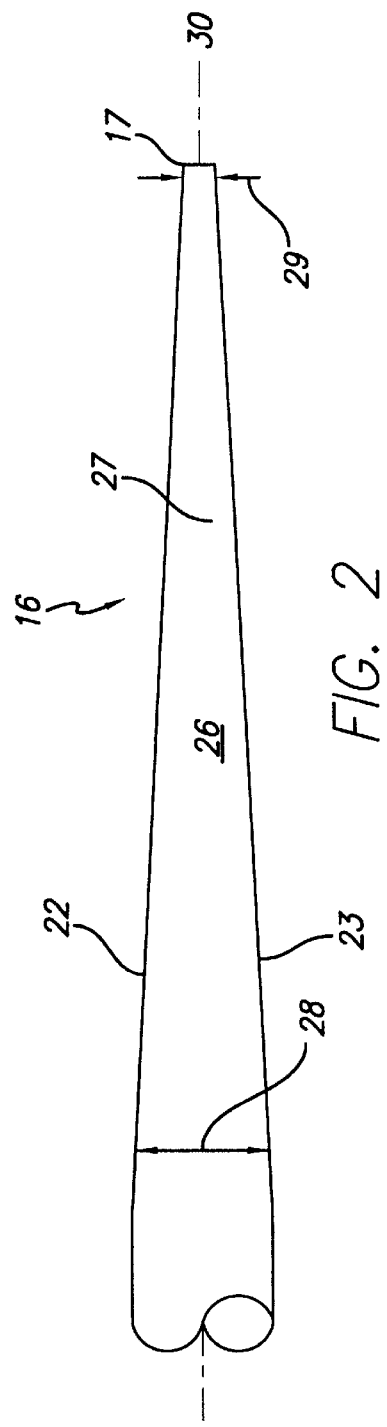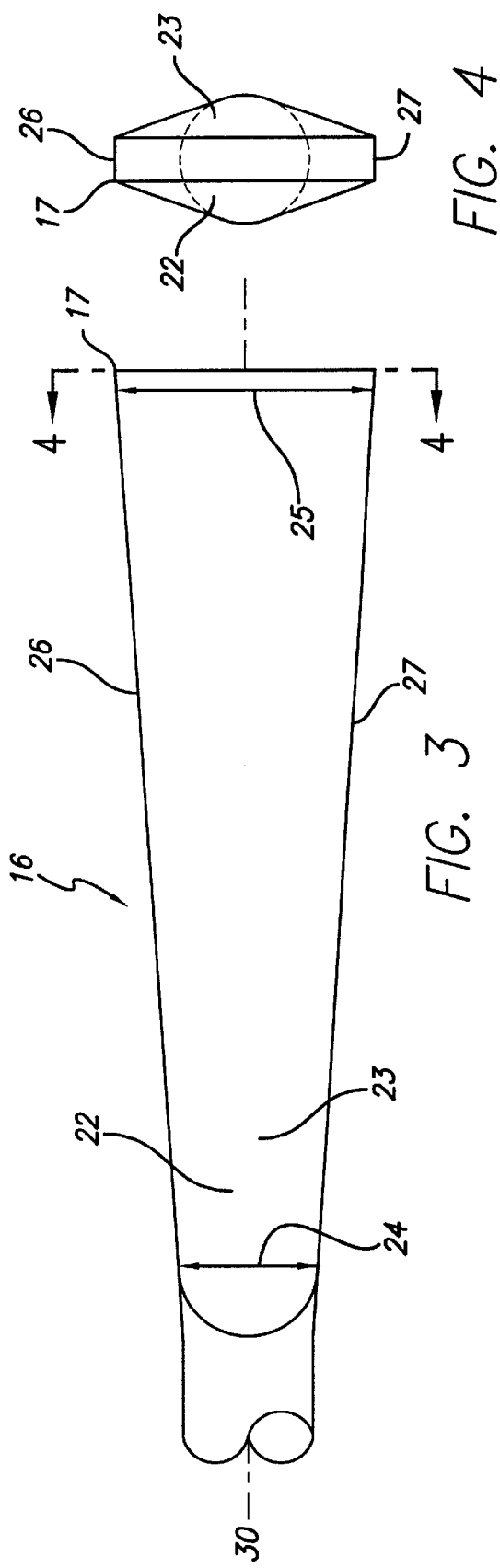

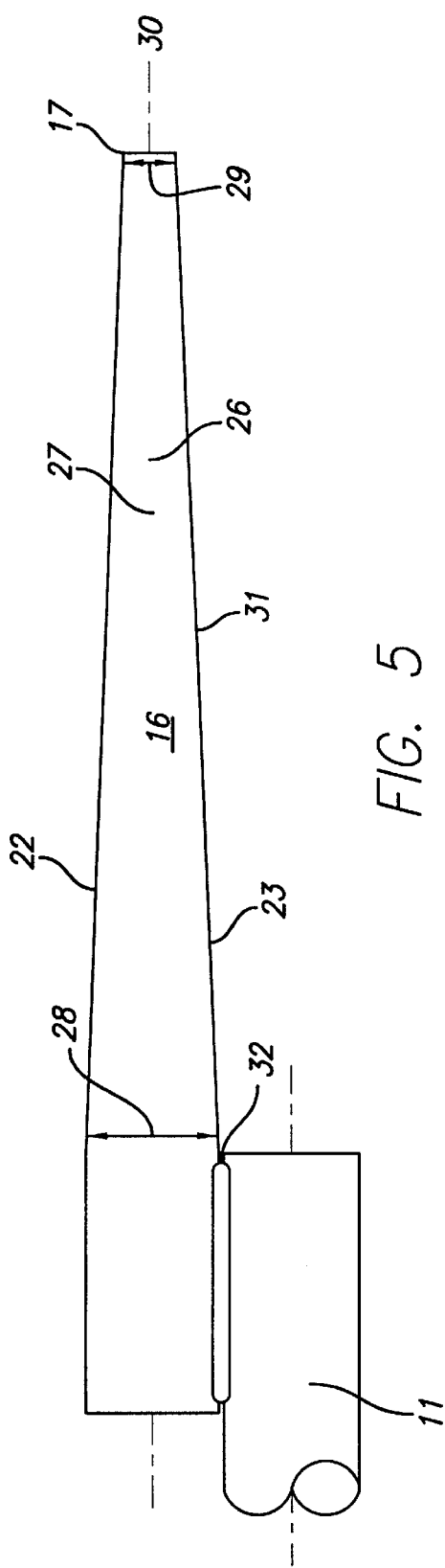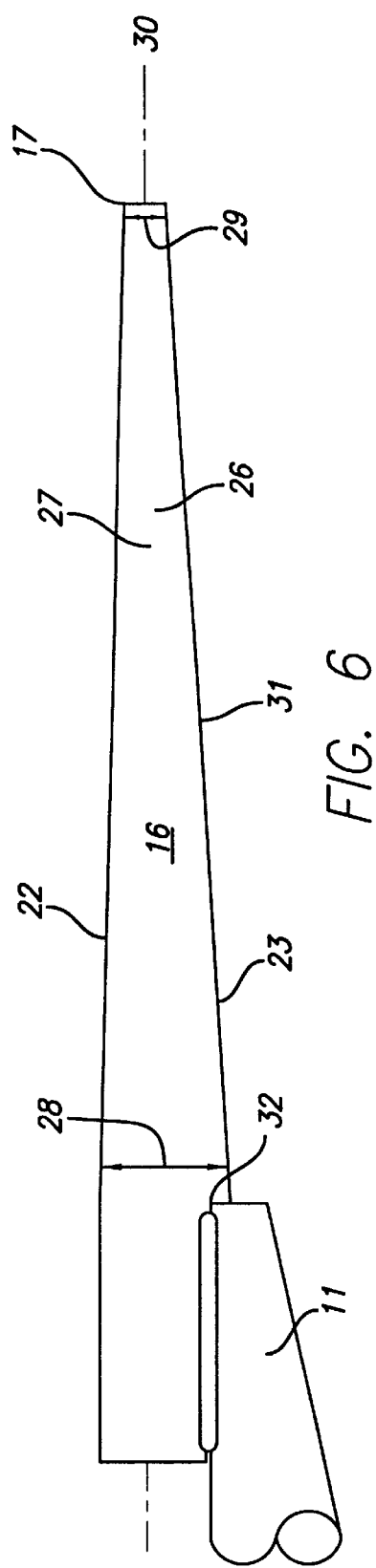

GUIDEWIRE WITH TAPERED FLEXIBLE CORE SEGMENT

RELATED APPLICATIONS

This application is a Continuation-In-Part of pending U.S. patent application Ser. No. 09/224,451, entitled "Guidewire With Smoothly Tapered Segment", filed by the same inventive entity on Dec. 31, 1998; which application is the basis for the International Application PCT/US99/30771, filed Dec. 21, 1999. The priority of each of these applications is claimed pursuant to 35 USC §119 and §120. Both applications are incorporated herein by reference in their entirety.

BACKGROUND OF THE INVENTION

This invention relates to the field of guidewires for advancing intraluminal devices such as stent delivery catheters, balloon dilatation catheters, atherectomy catheters and the like within body lumens.

In a typical percutaneous coronary procedure, a guiding catheter having a pre-formed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guidewire is first advanced by itself through the guiding catheter until the distal tip of the guidewire extends beyond the arterial location where the procedure is to be performed. Then a rapid exchange type catheter, such as described in U.S. Pat. No. 5,061,273 (Yock) is mounted onto the proximal portion of the guidewire which extends out of the proximal end of the guiding catheter which is outside of the patient. The catheter is advanced over the guidewire, while the position of the guidewire is fixed, until the operative element on the rapid exchange type catheter is disposed within the arterial location where the procedure is to be performed. After the procedure is performed, the rapid exchange type catheter may be withdrawn from the patient over the guidewire or the guidewire repositioned within the coronary anatomy for an additional procedure.

A guidewire may also be used in conjunction with the delivery of an intracoronary stent. One method and system involves disposing a compressed or otherwise small diameter stent about an expandable member such as a balloon on the distal end of a catheter, advancing the catheter through the patient's vascular system over a guidewire until the stent is in the desired location within a blood vessel. The expandable member on the catheter may then be expanded to expand the stent within the blood vessel. The dilated expandable member is then contracted and the catheter withdrawn, leaving the expanded stent within the blood vessel, holding the passageway thereof open. This latter method and system can be used concurrently with balloon angioplasty or subsequent thereto.

Further details of guidewires, and devices associated therewith for various interventional procedures can be found in U.S. Pat. No. 4,748,986 (Morrison et al.); U.S. Pat. No. 4,538,622 (Samson et al.); U.S. Pat. No. 5,135,503 (Abrams); U.S. Pat. No. 5,341,818 (Abrams et al.); and U.S. Pat. No. 5,345,945 (Hodgson, et al.) which are hereby incorporated herein in their entirety by reference thereto.

Conventional guidewires for angioplasty, stent delivery, atherectomy and other intravascular procedures usually have an elongate core member with one or more segments near the distal end thereof which taper distally to smaller cross sections. A flexible body member, such as a helical coil or a tubular body of polymeric material, is typically disposed about and secured to at least part of the distal portion of the core member. A flexible core segment, which may be the distal extremity of the core member or a separate shapeable ribbon which is secured to the distal extremity of the core member extends through the flexible body and is secured to the distal end of the flexible body by soldering, brazing or welding, or an adhesive in the case of polymeric flexible bodies which forms a rounded distal tip. The leading tip is highly flexible and will not damage or perforate the vessel and the portion behind the distal tip is increasingly stiff which better supports a balloon catheter or similar device.

The flexible core segment or ribbon of a typical guidewire is a small diameter wire which has been flattened to a relatively constant transverse profile. Flattening of the flexible core segment facilitates the shapability of the member. However, a flexible core segment having a constant transverse profile or flexibility can be subject to prolapse during use. Prolapse occurs when the flexible core segment gets bent back on itself in a constrained lumen and is difficult to straighten out with proximal manipulation. The present invention satisfies these and other needs.

SUMMARY OF THE INVENTION

The present invention is directed to a guidewire having an elongate core member with a proximal core section and a distal core section, and a flexible body disposed about and secured to at least a portion of the distal core section. The guidewire has an elongated, preferably shapeable flexible core segment which is secured to or which is formed as part of the distal core section and which is secured to the distal end of the flexible body disposed about the distal core section. The distal core section may have one or more tapered sections proximal to the flexible core segment which have distally decreasing tapers with substantially round transverse cross sections.

The tapered, preferably shapeable flexible core segment has a double reverse taper, i.e. a first transverse dimension which distally tapers over a substantial length thereof from a first value to a second smaller value and a second transverse dimension which distally tapers over essentially the same length of the flexible core segment from a first value to a second larger value, i.e. flares outwardly. The length of the tapered flexible core segment is about 1 to about 12 cm, preferably about 2 to about 10 cm. At least 50%, preferably at least 75% of the length of the tapered flexible core segment is tapered as described above. The distal most portion of the flexible core segment (i.e. up to about 15 mm) may be flat with one or both of the opposed faces being parallel. The tapers may be straight or curved.

The flexible core segment preferably has two pairs of opposing faces which are essentially the mirror image of each other. In one of the pairs the opposing faces converge toward each other while in the other pair the opposing faces diverge from each other.

The flexible core segment may be formed integrally or out of the distal extremity of the distal core section or may be formed as a distinct structural component or shaping ribbon which needs to be mounted in a suitable manner to the distal core section, e.g. by welding, brazing, soldering, adhesive bonding, mechanical connections and other known mounting processes. The flexible core segment may by formed from round or flattened wire and may be coined or rolled or otherwise plastically deformed, e.g. cold forged, to a desired shape and sectional profile. When the flexible core segment is a separate member from the core member, it may be formed before or after it is secured to the core member.

The flexible body member is disposed about the flexible core segment, preferably along its entire length and may take the form of a helical coil, polymer jacket, or the like. The distal end of the flexible body member is secured to the distal end of the flexible core segment and an intermediate portion of the flexible body member is preferably secured to the distal core section proximal to the tapered flexible core segment.

The double taper of the flexible core segments on the distal part of the guidewire reduces the likelihood of prolapsing or kinking of the guidewire's distal extremity during procedures and may be used to provide a controlled longitudinal variation and transition in flexibility of the core segment to the distal tip of the guidewire. A flexible body member, such as a helical coil or a tubular plastic member, having a proximal end and a distal end is typically disposed about and secured to the distal section of the elongate core member.

The taper geometry of the flexible segment may be modeled mathematically. Specific taper or face contours may be selected in keeping with the principles of the invention to achieve optimum performance for specific usage requirements. These and other advantages of the invention will become more apparent from the following detailed description of the invention when taken in conjunction with the accompanying exemplary drawings.

BRIEF DESCRIPTION OF THE DRAWINGS

FIG. 2 is an enlarged elevational view of a portion of the distal core section of the guidewire shown in FIG. 1.

FIG. 3 is an enlarged elevational view of a portion of the distal core section of the guidewire shown in FIG. 1 taken 90° from the view shown in FIG. 2

FIG. 4 is an end view of the embodiment of FIG. 3, shown as viewed from line 4—4 in FIG. 3.

FIG. 5 is an elevational view of an alternative core member for a guidewire such as shown in FIG. 1 having separate flexible core segment having features of the invention, mounted onto the distal extremity of a guidewire core member.

FIG. 6 is an elevational view of another alternative core member similar to that shown in FIG. 5 but which has been shaped after the flexible core segment is secured to the core member.

DETAILED DESCRIPTION OF THE INVENTION

Figure 1:
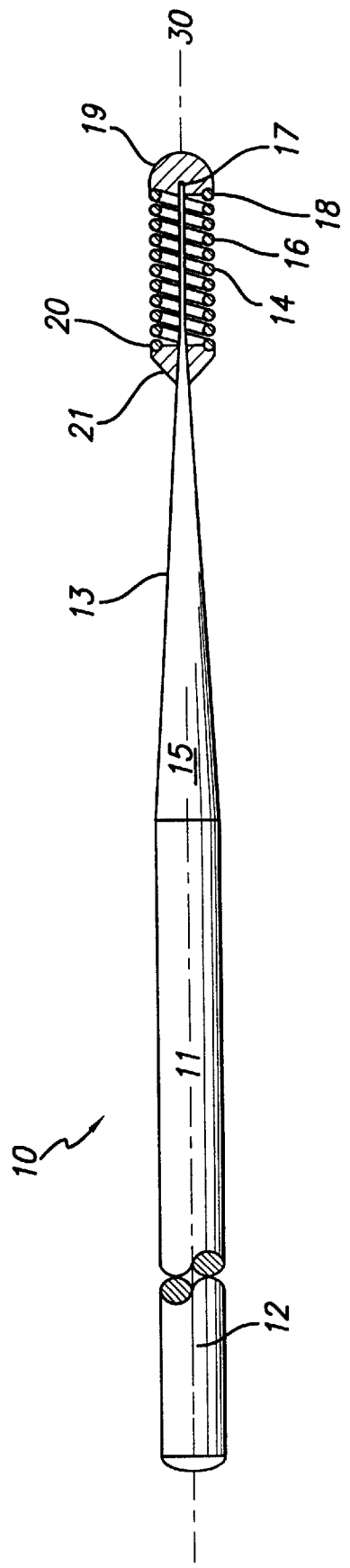
FIG. 1 is an elevation view, partially in section, of a guidewire embodying features of the invention.

FIG. 1 is an elevational view of an embodiment of a guidewire 10 which embodies features of the invention, and which includes an elongated core member 11 with a proximal core section 12, a distal core section 13, and a flexible body member or coil 14 which is disposed about and fixed to the distal core section 13. The distal core section 13 has a tapered core segment 15 and a flexible core segment 16 which is distally contiguous to the tapered core segment 15 and a distal end 17 which is secured to the distal end 18 of the coil 14 by a rounded body of solder or weld 19. The proximal end 20 of the coil 14 is similarly bonded or secured to the distal core section 13 by a body of solder 21.

Thus, it may be seen in FIGS. 2 and 3 that the thickness of the flexible core segment 16 decreases distally as measured between faces 26 and 27, while the width of the flexible segment 16 increases distally as measured between side faces 22 and 23. The cross section of the flexible core segment may be generally rectangular in all or in a portion of its length. While not shown, a transition may be provided which tapers from the round transverse cross-section of the proximal portion of the flexible tapered section 16 to the rectangular cross-section of the tapered portion, so as to create a smooth transition at the proximal end of the flexible segment 16. This results in a smooth decrease in stiffness in one direction but a smooth increase in stiffness in a second direction perpendicular to the first direction. While each of the tapered faces 24–27 is shown as having a longitudinal contour that is substantially straight, these tapered faces may have a curved longitudinal contour. The side face 24 is shown generally as a mirror image of the side face 25 about the longitudinal axis 30 and the top face 26 is shown generally as a mirror image of the bottom face 27 about the axis 30. However, the opposed faces need not be symmetrical.

In FIGS. 1–4, the flexible core segment 16 is shown as being an integral part of the distal core section 13. In FIG. 5 and 6, the flexible core segment 16 is shown as a separate shaping member 31 which has been secured to the distal end of the core member 11 by solder or weldment 32. The opposing pairs of faces are the same as that shown in FIGS. 2–4 and are provided with the same reference numbers. In FIG. 5 the shaping member 31 is shaped before being secured to the core member 11, whereas, in FIG. 6 the shaping member 31 and the distal tip of the core member 11 has been shaped after being joined together.

The flexible segment 16 has a length typically ranging about 1 to about 12 cm, preferably about 2 to about 10 cm, although longer segments may be used. At least 50% and preferably at least 75% of the length of the flexible segment 16 is tapered. The form of taper of the flexible segment 16 provides a controlled longitudinal variation and transition in flexibility of the distal core section. The first transverse or thickness dimension of the taper at a proximal portion of the flexible segment 16 is about 0.001 to about 0.0035 inch (0.025–0.09 mm), preferably about 0.0015 to about 0.0025 inch (0.04–0.06 mm) which tapers to about 0.0005 to about 0.0025 inch (0.01–0.06 mm), preferably about 0.0007 to about 0.0015 inch (0.02–0.04 mm) at the distal portion. The second transverse dimension or width, perpendicular to the first transverse dimension, of the taper at a proximal portion of the flexible segment 16 is about 0.001 to about 0.0035 inch (0.025–0.09 mm), preferably about 0.0015 to about 0.0025 inch (0.04–0.06 mm) which flares to about 0.002 to about 0.008 inch (0.05–0.2 mm), preferably about 0.003 to about 0.006 inch (0.08–0.15 mm).

The multiple tapers or faces of the flexible core segment 16 are preferably formed by impact forging or rolling a wire or ribbon of suitable dimensions, but other methods may be employed.

The flexible core segment 16, which is shown in more detail in FIGS. 2–5, has a first pair of opposed faces 22 and 23 which taper distally from a first transverse dimension 24 to a larger second transverse dimension 25 and a second pair of opposed faces 26 and 27 which taper distally from a first transverse dimension 28 to a smaller transverse dimension 29. The first transverse dimensions 24 and 28 of the first and second pairs of opposed faces respectively may have same value or different values. Thus, flexible core segment 16 tapers to become progressively thinner in one transverse direction and wider in a second transverse direction as the distal end 17 is approached. This results in a smooth decrease in stiffness in one direction but a smooth increase in stiffness in a second direction perpendicular to the first direction. While each of the tapered faces 22–27 is shown as having a longitudinal contour that is substantially straight, these tapered faces may have a curved longitudinal contour. The side faces 22, 23 may be bowed outward as indicated by the dashed circle in FIG. 4 to include convex curves. The side face 22 is shown generally as a mirror image of the side face 23 about the longitudinal axis 30 and the top face 26 is shown generally as a mirror image of the bottom face 27 about the axis 30. However, the opposed faces need not be symmetrical.

The flexible core segment may vary in length from about 0.25 cm to about 10 cm, although both shorter and longer segments are may be desirable in some procedures. The width and thickness at each cross sectional portion may be varied to provide the desired stiffness along the distal portion of the guidewire.

The distal section 13 may also have more than one tapered segment 15 which have typical distally decreasing tapers with substantially round transverse cross sections, such as described in U.S. patent application Ser. No. 08/868,764, filed Jun. 4, 1997 (Cornish, et al.) entitled STEERABLE GUIDEWIRE WITH ENHANCED DISTAL SUPPORT, which is hereby incorporated by reference in its entirety.

The core member 11 may be formed of stainless steel, NiTi alloys or combinations thereof such as described in U.S. Pat. No. 5,341,818 (Abrams et al) which has been incorporated herein. Other materials such as the high strength alloys described in U.S. Pat. No. 5,636,641 (Fariabi), entitled HIGH STRENGTH MEMBER FOR INTRACORPOREAL USE, which is incorporated herein by reference, may also be used. The core member 11 may be optionally coated with a lubricious coating such as a fluoropolymer, e.g. TEFLON ® available from DuPont, which extends at least the length of the proximal core section 12. The distal section 13 is also provided with a lubricous coating, such as a MICROGLIDE ™ coating (a silicone material) used by the present assignee, Advanced Cardiovascular Systems, Inc. on many of its commercially available guidewires. Hydrophilic coatings may also be employed.

The overall length and diameter of guidewire 10 may be varied to suit the particular procedures in which it is to be used and the materials from which it is constructed. The length of the guidewire 10 generally ranges from about 65 cm to about 320 cm, more typically ranging from about 160 cm to about 200 cm. Commercially available guidewires for coronary anatomy, typically have lengths of about 175 cm or about 190 cm for the coronary anatomy. Guidewire diameters generally range from about 0.008 in. to about 0.035 in. (0.2 to 0.9 mm), more typically ranging from about 0.01 in. to about 0.018 in. (0.25 to 0.55 mm). Commercially available guidewires for coronary use are typically about 0.01, 0.012 and 0.014 inch (0.25, 0.3 and 0.036 mm) in diameter.

The wire from which the coil 14 is made generally has a transverse diameter of about 0.001 to about 0.004 inch (0.025–0.1 mm), preferably about 0.002 to about 0.003 inch (0.05–0.008 mm). Multiple turns of the distal portion of coil 14 may be expanded to provide additional flexibility. The helical coil 14 may have a diameter or transverse dimension that is about the same as the proximal core section 12. The coil 14 may have a length of about 2 to about 40 cm or more, preferably about 2 to about 10 cm in length. The coil 14 may at least in part be formed of a suitable radiopaque material such as platinum, palladium or alloys thereof or formed of other material such as stainless steel and coated with a radiopaque material such as gold. The coil 14 may be replaced with a flexible body member formed of a polymeric material such as polyimide, polyethylene, polyurethane, polytetrafluoroethylene (PTFE), expanded polytetrafluoroethylene (ePTFE) and other similar materials.

While particular forms of the invention have been illustrated and described, it will be apparent that various modifications can be made without departing from the scope of the invention. Accordingly, it is not intended that the invention be limited, except as by the appended claims. Moreover, those skilled in the art will recognize that a feature found in one embodiment may be utilized in another embodiment. Terms such as element, member, section, segment, body, device and words of similar import when used herein shall not be construed as invoking the provisions of 35 U.S.C. §112(6) unless the following claims expressly use the term "means" or "step" followed by a particular function.

What is claimed is:

1. A guidewire for advancing intracorporeal devices to a desired location within a patient's body, comprising:
   a. an elongate core member with a proximal core section and a distal core section with an elongated flexible core segment, the flexible core segment having a first transverse dimension tapering distally from a first value to a second smaller value and having a second transverse dimension tapering distally from a first value to a second larger value, wherein at least one of a pair of opposed faces containing the second transverse dimension at the flexible core segment includes convex curves encompassing a cross-sectional radius of the flexible core segment; and
   b. a flexible body disposed about and secured to a portion of the distal core section.

2. The guidewire of claim 1 wherein a first pair of opposed faces taper in width distally such that each has a transverse dimension that is greater at their proximal ends than at their distal ends.

3. The guidewire of claim 1 wherein a second pair of opposed faces taper in width distally such that each has a transverse dimension which is smaller at their proximal ends than at their distal ends.

4. The guidewire of claim 1 wherein at least one of a first pair of opposed faces has a longitudinal contour that is substantially straight.

5. The guidewire of claim 1 wherein a first pair of opposed faces have a transverse dimension greater than a corresponding transverse dimension of the second pair of opposed faces along a substantial length of the flexible core segment.

6. The guidewire of claim 1 wherein the pair of opposed faces has a substantially non-semicircular shape.

7. The guidewire of claim 1 wherein the elongate flexible core segment is a member separate from the core member and which has a distal end secured to the distal end of the flexible body disposed about the distal core section and a proximal end secured to the core member.

8. The guidewire of claim 1 wherein the elongated flexible core segment has a length of about 1 to about 12 cm.

9. The guidewire of claim 1 wherein the elongated flexible core segment has a length of about 2 to about 10 cm.

10. The guidewire of claim 1 wherein at least 50% of the length of the flexible core segment is tapered.

11. The guidewire of claim 1 wherein at least 75% of the length of the flexible core segment 16 is tapered.

12. The guidewire of claim 1 wherein the taper of the flexible core segment is configured to provide a controlled longitudinal variation and transition in flexibility.

13. The guidewire of claim 1 wherein the first transverse dimension of the taper at a proximal portion of the flexible core segment is about 0.001 to about 0.0035 inch (0.025–0.09 mm).

14. The guidewire of claim 1 wherein the first transverse dimension of the taper at the proximal portion of the flexible core segment is about 0.0015 to about 0.0025 inch (0.04–0.06 mm).

15. The guidewire of claim 13 wherein the first transverse dimension tapers to about 0.0005 to about 0.0025 inch (0.01–0.06 mm).

16. The guidewire of claim 1 wherein he first transverse dimension tapers to about 0.0007 to about 0.0015 inch (0.02–0.04 mm).

17. The guidewire of claim 1 wherein the second transverse dimension perpendicular to the first transverse dimension, of the taper at a proximal portion of the flexible core segment is about 0.001 to about 0.0035 inch (0.025–0.09 mm).

18. The guidewire of claim 1 wherein the second transverse dimension perpendicular to the first transverse dimension, of the taper at a proximal portion of the flexible core segment is about 0.0015 to about 0.0025 inch (0.04–0.06 mm).

19. The guidewire of claim 18 wherein the second transverse dimension of the flexible core segment flares to about 0.002 to about 0.008 inch (0.05–0.2 mm).

20. The guidewire of claim 18 wherein the second transverse dimension of the flexible core segment flares to about 0.003 to about 0.006 inch (0.08–0.15 mm).

21. A guidewire comprising:
   a. an elongate core member with a proximal core section and a tapered distal core section;
   b. a flexible body disposed about and secured to at least a portion of the distal core section; and
   c. an elongated flexible core segment secured to the distal core section which has a distal end secured to the distal end of the flexible body disposed about the distal core section, which has a first transverse dimension tapering distally from a first value to a second smaller value and which has a second transverse dimension perpendicular to the first dimension tapering distally from a first value to a second larger value, wherein a pair of opposed faces containing the second transverse dimension at the elongated flexible core segment include convex curves extending to a radius of the elongated flexible core segment.

22. The guidewire of claim 21 wherein a first pair of opposed faces have a transverse dimension greater than a corresponding transverse dimension of the second pair of opposed faces along a substantial length of the flexible core segment.

23. The guidewire of claim 21 wherein the elongated flexible core segment has a length of about 1 to about 12 cm.

24. The guidewire of claim 21 wherein the elongated flexible core segment has a length of about 2 to about 10 cm.

25. The guidewire of claim 21 wherein at least 50% of the length of the flexible core segment is tapered.

26. The guidewire of claim 21 wherein at least 75% of the length of the flexible core segment 16 is tapered.

27. The guidewire of claim 21 wherein the taper of the flexible core segment is configured to provide a controlled longitudinal variation and transition in flexibility.

28. The guidewire of claim 21 wherein the first transverse dimension of the taper at a proximal portion of the flexible core segment is about 0.001 to about 0.0035 inch (0.025–0.09 mm).

29. The guidewire of claim 21 wherein the first transverse dimension of the taper at the proximal portion of the flexible core segment is about 0.0015 to about 0.0025 inch (0.04–0.06 mm).

30. The guidewire of claim 21 wherein the first transverse dimension tapers to about 0.0005 to about 0.0025 inch (0.01–0.06 mm).

31. The guidewire of claim 21 wherein the first transverse dimension tapers to about 0.0007 to about 0.0015 inch (0.02–0.04 mm).

32. The guidewire of claim 21 wherein the second transverse dimension perpendicular to the first transverse dimension, of the taper at a proximal portion of the flexible core segment is about 0.001 to about 0.0035 inch (0.025–0.09 mm).

33. The guidewire of claim 21 wherein the second transverse dimension perpendicular to the first transverse dimension, of the taper at a proximal portion of the flexible core segment is about 0.0015 to about 0.0025 inch (0.04–0.06 mm).

34. The guidewire of claim 21 wherein the second transverse dimension of the flexible core segment flares to about 0.002 to about 0.008 inch (0.05–0.2 mm).

35. The guidewire of claim 21 wherein the second transverse dimension of the flexible core segment flares to about 0.003 to about 0.006 inch (0.08–0.15 mm).

36. A guidewire for advancing intracorporeal devices to a desired location within a patient's body, comprising:
   an elongate core member having a proximal core section and a distal core section, wherein the distal core section includes a flexible core segment;
   the flexible core segment having a diverging taper contained in a first plane, and a converging taper contained in a second plane;
   opposed faces contained in the first plane and formed at the flexible core segment, wherein the opposed faces include convex curves extending to a radius of the flexible core segment.

* * * * *

UNITED STATES PATENT AND TRADEMARK OFFICE
CERTIFICATE OF CORRECTION

PATENT NO.    : 6,491,648 B1
DATED         : December 10, 2002
INVENTOR(S)   : Wayne E. Cornish et al.

It is certified that error appears in the above-identified patent and that said Letters Patent is hereby corrected as shown below:

Columns 3 and 4,
Lines 64-67 and 1-8 respectively, ending with "segment 16.", move to Column 4, line 54.

Column 4,
Delete lines 8-18, beginning with "This results…" and ending with "cal."

Columns 4 and 5,
Lines 54-67 and 1-10 respectively, beginning with "The flexible…" and ending with "symmetrical.", move to Column 3, line 64.

Signed and Sealed this

Fifteenth Day of April, 2003

JAMES E. ROGAN
*Director of the United States Patent and Trademark Office*